(12) United States Patent
Gregerson et al.

(10) Patent No.: US 9,978,157 B2
(45) Date of Patent: May 22, 2018

(54) METHOD AND SYSTEM FOR X-RAY CT IMAGING

(71) Applicant: Mobius Imaging, LLC, Shirley, MA (US)

(72) Inventors: Eugene A. Gregerson, Bolton, MA (US); Michael Allen, Boxborough, MA (US); Paul Sebring, Townsend, MA (US); Jonathan Yuen, Arlington, MA (US); Kenneth L. Hilts, Merrimac, MA (US)

(73) Assignee: MOBIUS IMAGING, LLC, Shirley, MA (US)

( * ) Notice: Subject to any disclaimer, the term of this patent is extended or adjusted under 35 U.S.C. 154(b) by 0 days. days.

(21) Appl. No.: 15/401,631

(22) Filed: Jan. 9, 2017

(65) Prior Publication Data

US 2017/0124731 A1 May 4, 2017

Related U.S. Application Data

(60) Continuation of application No. 14/810,529, filed on Jul. 28, 2015, now Pat. No. 9,576,378, which is a
(Continued)

(51) Int. Cl.
*A61B 6/03* (2006.01)
*G01T 1/24* (2006.01)
(Continued)

(52) U.S. Cl.
CPC ............ *G06T 11/003* (2013.01); *A61B 6/035* (2013.01); *A61B 6/4233* (2013.01);
(Continued)

(58) Field of Classification Search
CPC ......... A61B 6/035; A61B 6/5205; A61B 6/56; A61B 6/563; G01T 1/17; G01T 1/24; G01T 1/243; G01T 1/247; H05G 1/08
See application file for complete search history.

(56) References Cited

U.S. PATENT DOCUMENTS 5,742,060 A 4/1998 Ashburn
6,194,726 B1 2/2001 Pi et al.
(Continued)

FOREIGN PATENT DOCUMENTS

DE 4116381 C1 7/1992
JP 2006-075489 A 3/2006
(Continued)

OTHER PUBLICATIONS

International Search Report and the Written Opinion of the International Searching Authority in International Application No. PCT/US2013/048631 dated Sep. 26, 2013.
(Continued)

*Primary Examiner* — Thomas R Artman
(74) *Attorney, Agent, or Firm* — The Marbury Law Group, PLLC

(57) ABSTRACT

Methods and systems for performing x-ray computerized tomographic (CT) reconstruction of imaging data on a rotatable portion of the system, such as a ring-shaped rotor. The rotor may include an x-ray source, and x-ray detector system and a processor, coupled to the detector system, for performing tomographic reconstruction of imaging data collected by the detector system.

18 Claims, 10 Drawing Sheets

Related U.S. Application Data division of application No. 13/930,881, filed on Jun. 28, 2013, now Pat. No. 9,111,379.

(60) Provisional application No. 61/665,482, filed on Jun. 28, 2012.

(51) Int. Cl.
*G06T 11/00* (2006.01)
*A61B 6/00* (2006.01)
*G06T 7/00* (2017.01)
*G06T 1/20* (2006.01)

(52) U.S. Cl.
CPC .......... *A61B 6/4283* (2013.01); *A61B 6/5205* (2013.01); *A61B 6/563* (2013.01); *G01T 1/243* (2013.01); *G01T 1/247* (2013.01); *G06T 1/20* (2013.01); *G06T 7/0012* (2013.01); *G06T 2207/10081* (2013.01)

(56) References Cited

U.S. PATENT DOCUMENTS

| | | | |
|---|---|---|---|
| 6,327,330 B1 | 12/2001 | Peter | |
| 6,470,067 B1 | 10/2002 | Harding | |
| 6,541,763 B2 | 4/2003 | Lingren et al. | |
| 6,801,594 B1* | 10/2004 | Ali | A61B 6/032 378/114 |
| 7,006,592 B2* | 2/2006 | Ali | A61B 6/032 378/4 |
| 9,111,379 B2 | 8/2015 | Gregerson et al. | |
| 9,576,378 B2* | 2/2017 | Gregerson | G06T 11/003 |
| 2003/0031290 A1 | 2/2003 | Sugihara et al. | |
| 2004/0131144 A1 | 7/2004 | Nishide et al. | |
| 2004/0247070 A1 | 12/2004 | Ali et al. | |
| 2005/0096523 A1 | 5/2005 | Vass et al. | |
| 2006/0261275 A1 | 11/2006 | Stears et al. | |
| 2007/0041488 A1 | 2/2007 | Hoheisel et al. | |
| 2007/0165770 A1 | 7/2007 | Vogtmeier | |
| 2009/0010381 A1 | 1/2009 | Schlomka | |
| 2009/0129539 A1 | 5/2009 | Licato et al. | |
| 2009/0279660 A1 | 11/2009 | Takamatsu et al. | |
| 2014/0003572 A1 | 1/2014 | Gregerson et al. | |
| 2014/0093039 A1 | 4/2014 | Yang et al. | |
| 2015/0332484 A1 | 11/2015 | Gregerson et al. | |

FOREIGN PATENT DOCUMENTS

| | | |
|---|---|---|
| JP | 2011-154031 A | 8/2011 |
| JP | 2011-220982 A | 11/2011 |
| JP | 2012-081181 A | 4/2012 |
| KR | 10-2012-0003900 A | 1/2012 |

OTHER PUBLICATIONS

International Preliminary Report on Patentability (Chapter 1 of the Patent Cooperation Treaty) in International Application No. PCT/US2013/048631 dated Jan. 8, 2015.

Communication pursuant to Rules 702(2) and 70(a)(2) EPC in suplementary European Search Report in Application No. 13810875.8-0 1666/2866666 for PCT/US2013/048631 dated Mar. 22, 2016.

Extended European Search Report in Application NO. 13810875.8-0 1666/2866666 for PCT/US2013/048631 dated Mar. 4, 2016.

\* cited by examiner

METHOD AND SYSTEM FOR X-RAY CT IMAGING

RELATED APPLICATIONS

This application is a continuation application of U.S. application Ser. No. 14/810,529, filed Jul. 28, 2015, which is a division application of U.S. application Ser. No. 13/930,881, filed Jun. 28, 2013, which claims the benefit of priority to U.S. Provisional Application No. 61/665,482, filed Jun. 28, 2012, the entire contents of all of which are incorporated herein by reference.

BACKGROUND

Conventional 3D computed tomography (CT) x-ray scanning systems are large, fixed-bore devices that are typically located in the radiology department of a hospital or other medical facility. In a typical device, the patient is loaded into the bore through the front or rear of the device, and a rotatable component, such as a large drum to which imaging components are secured, is rotated around the patient to collect imaging data. The collected imaging data is exported off of the rotating portion, such as via a cable or slip ring system, to an external computer or workstation, where the collected data may be processed using a suitable tomographic algorithm to produce a three-dimensional tomographic reconstruction of a region of interest of the patient.

SUMMARY

Various embodiments include methods and systems for performing x-ray computerized tomographic (CT) reconstruction of imaging data on a rotatable portion of the system, such as a ring-shaped rotor. The rotor may include an x-ray source, and x-ray detector system and a processor, coupled to the detector system, for performing tomographic reconstruction of imaging data collected by the detector system.

Embodiments include methods for generating an x-ray CT reconstruction with an imaging system including an x-ray source and a detector mounted to a rotatable rotor, the method including generating an electronic representation of image data received at a plurality of detector elements of the detector while the rotor rotates, sending the electronic representation of the image data to a processor located on the rotor while the rotor is rotating, performing tomographic reconstruction of the image data using the processor located on the rotor, and transmitting the reconstruction from the rotor to an entity off the rotor.

Further embodiments include an x-ray CT system that includes an x-ray source, a detector, a memory, and a processor coupled to the memory and configured with processor-executable instructions for performing tomographic reconstruction of image data received from the detector, wherein the x-ray source, the detector, the memory and the processor are located on a rotor that rotates around an object being imaged.

Further embodiments include an x-ray CT system including means for generating an electronic representation of image data received at a plurality of detector elements of the detector while the rotor rotates, means for sending the electronic representation of the image data to a processor located on the rotor while the rotor is rotating, means for performing tomographic reconstruction of the image data using the processor located on the rotor, and means for transmitting the reconstruction from the rotor to an entity off the rotor.

Further embodiments include non-transitory computer-readable storage media having stored thereon processor executable instructions configured to cause a processor of a first detector module of an x-ray CT imaging system to perform operations including receiving an electronic representation of image data from a second detector module, appending an electronic representation of image data received at a plurality of detector elements of the first detector module to the electronic representation of image data received from the first detector module to generate a combined image data set, and transmitting the combined image data set from the from the first detector module.

BRIEF DESCRIPTION OF THE DRAWINGS

Other features and advantages of the present invention will be apparent from the following detailed description of the invention, taken in conjunction with the accompanying drawings of which.

DETAILED DESCRIPTION

This application is related to U.S. application Ser. No. 12/576,681, filed Oct. 9, 2009, now U.S. Pat. No. 8,118,488, U.S. application Ser. No. 13/025,566, filed Feb. 11, 2011, U.S. application Ser. No. 13/025,573, filed Feb. 11, 2011, U.S. application Ser. No. 13/441,555, filed Apr. 6, 2012, U.S. Provisional Application No. 61/658,650, filed Jun. 12, 2012, U.S. Provisional Application No. 61/659,609, filed Jun. 14, 2012, and U.S. Provisional Application No. 61/664,437, filed Jun. 26, 2012. The entire contents of all of these applications are hereby incorporated by reference for all purposes.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

Various embodiments include methods and systems for performing x-ray computerized tomographic (CT) reconstruction of imaging data on a rotatable portion of the system, such as a ring-shaped rotor. The rotor may include an x-ray source, and x-ray detector system and a processor, coupled to the detector system, for performing tomographic reconstruction of imaging data collected by the detector system.

Figure 1:
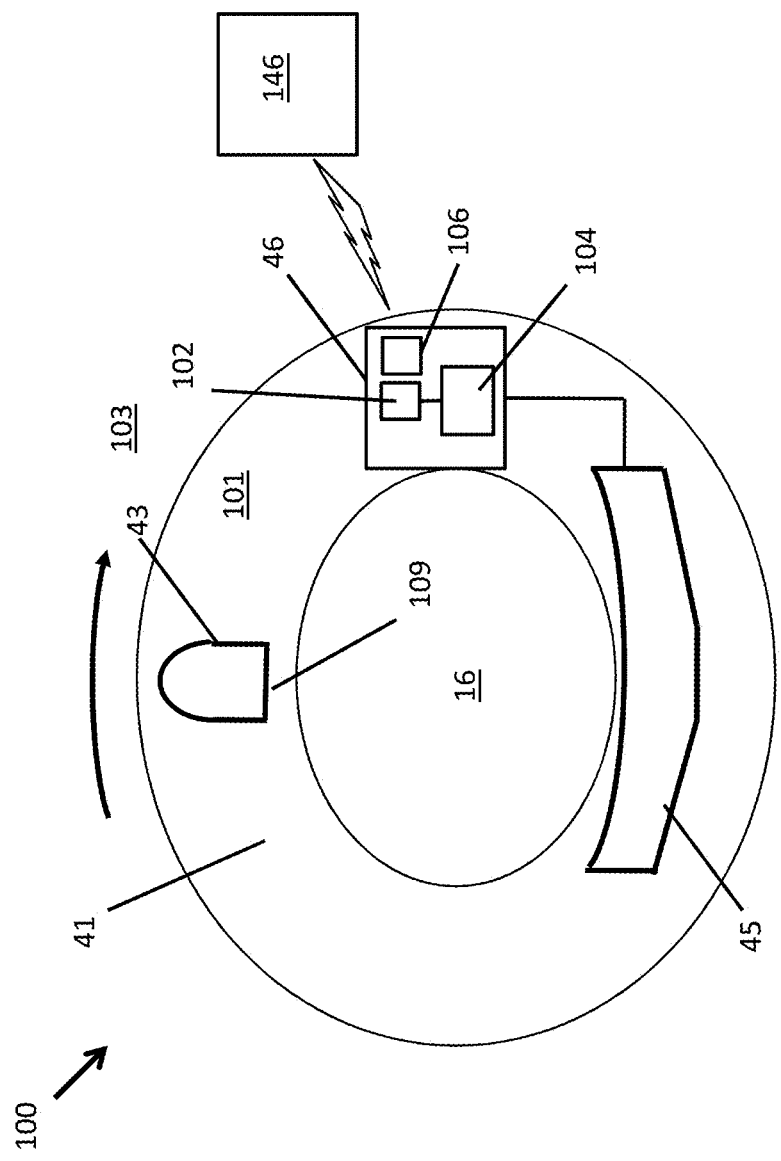
FIG. 1 is cross-sectional schematic illustration of an imaging system having a rotatable rotor with a processor for performing tomographic reconstruction of collected imaging data on the rotor.

FIG. 1 is a schematic cross-sectional view of an imaging system 100 according to one embodiment. The imaging system may include a rotatable portion 101 and a non-rotatable portion 103. The rotatable portion 101 may rotate around an image bore 16 within which an object, such as a human or animal patient, may be positioned, to obtain x-ray image data (e.g., raw x-ray projection data) corresponding to the object. The rotation of the rotatable portion 101 with respect to the non-rotatable portion is schematically illustrated by an arrow in FIG. 1. The rotatable portion 101 may comprise a rotor 41. The rotor 41 may be a rigid, ring-shaped component that may be located within a gantry (not illustrated). The gantry may be a substantially O-shaped housing that defines the bore 16, and may include a protective outer shell that defines an internal cavity within which the rotor 41 may rotate. The outer shell of the gantry may not rotate, and thus may be part of the non-rotatable portion 103 of the system. FIG. 1 schematically illustrates a number of components of the rotating portion 101, including an x-ray source 43, detector system 45, and computer 46, which may be mounted to rotor 41. Other components may be provided on the rotor 41, such as a high-voltage generator, a power supply (e.g., battery system), rotor drive system, and a docking system, which are not illustrated for clarity.

During an imaging scan, the rotor 41 rotates around an object positioned within the bore 16, while the imaging components such as the x-ray source 43 and detector system 101 operate to obtain imaging data (e.g., raw x-ray projection data) for an object positioned within the bore of the gantry, as is known, for example, in conventional X-ray CT scanners. The collected imaging data may be fed to an on-board computer 46, preferably as the rotor 41 is rotating, for performing x-ray CT reconstruction, as will be described in further detail below.

Various details of embodiments of an imaging system can be found in the above-referenced U.S. application Ser. Nos. 12/576,681, 13/025,566, 13/025,573, 13/441,555, 61/658,650, 61/659,609, and 61/664,437, which have been incorporated herein by reference. It will be understood that these embodiments are provided as illustrative, non-limiting examples of imaging systems suitable for use in the present methods and systems, and that the present systems and methods may be applicable to imaging systems of various types, now known or later developed.

Figure 3:
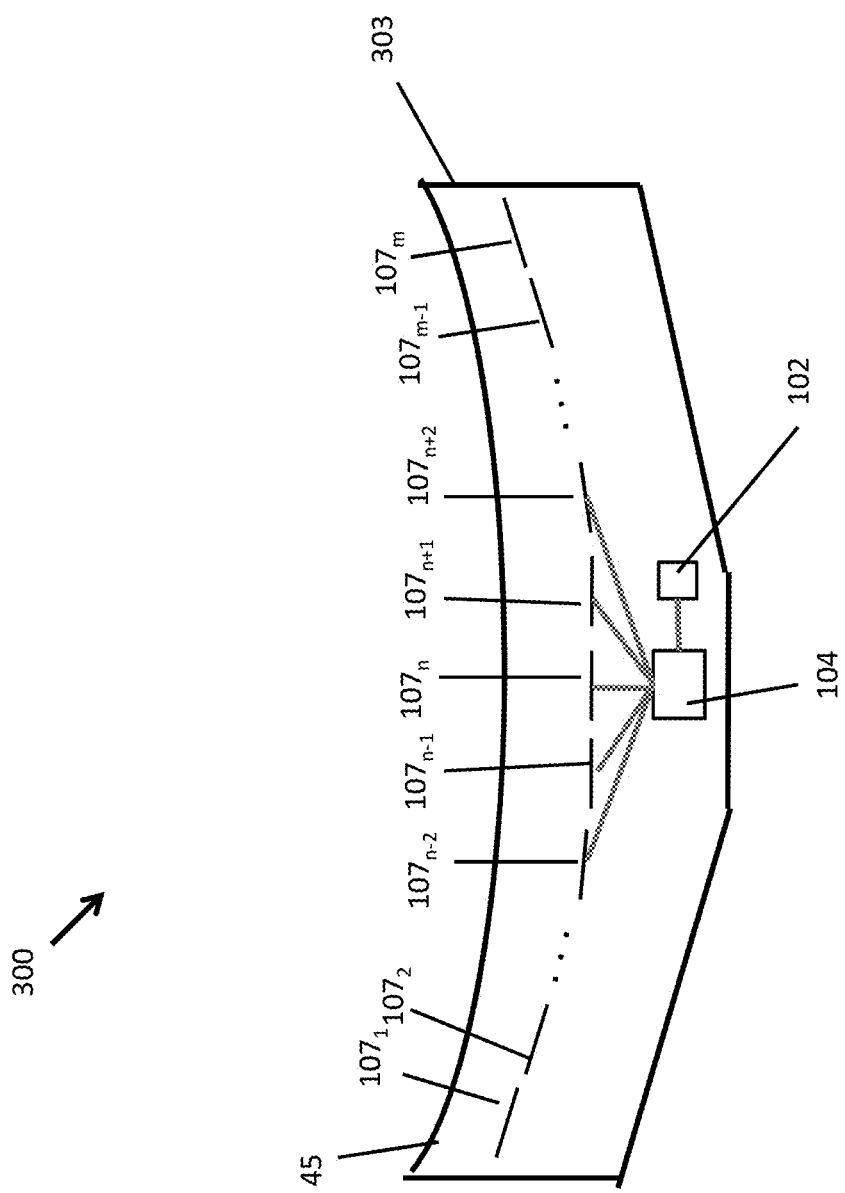
FIG. 3 is a cross-sectional schematic illustration of a detector system according to one embodiment.

The detector system 45 may include a plurality of x-ray sensitive detector elements, along with associated electronics, which may be enclosed in a housing or chassis 303 (FIG. 3). In one embodiment, the detector chassis has a width of 7¾ inches, a depth of between about 4-5 inches and a length of about 1 meter or more, such as about 43 inches. The detector chassis 303 may be a rigid frame, which may be formed of a metal material, such as aluminum, and which may be formed by a suitable machining technique. The detector system 45 may be mounted to the rotor 41 opposite an x-ray source 43, as is shown in FIG. 1. A plurality of x-ray-sensitive detector elements may be provided in the interior of the detector chassis 303 so that the detector elements face in the direction of the x-ray source 43. The detector chassis 303 may form a protective air- and light-tight shroud around the detector elements, so that unwanted air and light may not contaminate the sensitive components housed within the detector system 45.

In various embodiments, the individual detector elements may be located on a plurality of detector modules 107. FIG. 3 illustrates a plurality of detector modules 107 arranged within a chassis 303 of detector system 45. Each individual detector element, which may be for example, a cadmium tungstate ($CdWO_4$) material coupled to a photodiode, represents a pixel on a multi-element detector module 107. The modules 107 may be 2D element array, with for example 512 pixels per module (e.g., 32×16 pixels).

The detector system 45 may include one or more detector modules 107 mounted within the detector chassis 103. The module(s) 107 may be arranged along the length of the chassis 103 to form or approximate a semicircular arc, with the arc center coinciding with the focal spot 109 of the x-ray source 43 (see FIG. 1). In one embodiment, the detector system 45 includes thirty-one two-dimensional detector modules 107 positioned along the length of the chassis 103, and angled relative to each other to approximate a semicircular arc centered on the focal spot of the x-ray source. Each module 107 may be positioned such that the detector module 107 surface is normal to a ray extending from the x-ray focal spot 109 to the center pixel of the module 107.

It will be understood that the detector system 45 may include any number of detector modules 107 along the length of the detector. As shown in FIG. 3, for example, a detector may include "m" modules 107, where "m" may be any integer greater than or equal to 1. Further, each detector module 107 may include an arbitrary number of individual elements (pixels) in the module. Larger and/or a greater number of detector modules 107 may allow a larger diameter "backprojection" area around the isocenter of the imaging system, and thus may allow a larger cross-section of the object to be reconstructed.

As shown in the embodiment of FIG. 1, each module 107 may be electronically connected to a computer 46 which may be located on the rotatable portion 101 of the system (e.g., mounted to the rotor 41). The computer 46 may include a memory 104 and a processor 102 coupled to the memory, as is known in the art. The processor 102 may be configured to perform tomographic reconstruction of image data that is sent to the computer 46 from the detector modules 107. The computer 46 may also include a transmitter/transceiver 106, which may provide a wireless link to an external entity 108. The computer 46 may wirelessly transmit tomographic reconstruction data (e.g., 3D images of the object) to the external entity 108, which may be another computer, such as an external workstation, or a separate computer on the imaging system 100 (e.g., a computer on a gimbal that supports the gantry). In other embodiments, the computer 46 may transmit tomographic reconstruction data to another entity using a wired link (e.g., via a slip ring or cable connection to the non-rotating portion 103, or via a data dock to the non-rotating portion 103 in between scans).

Figure 2:
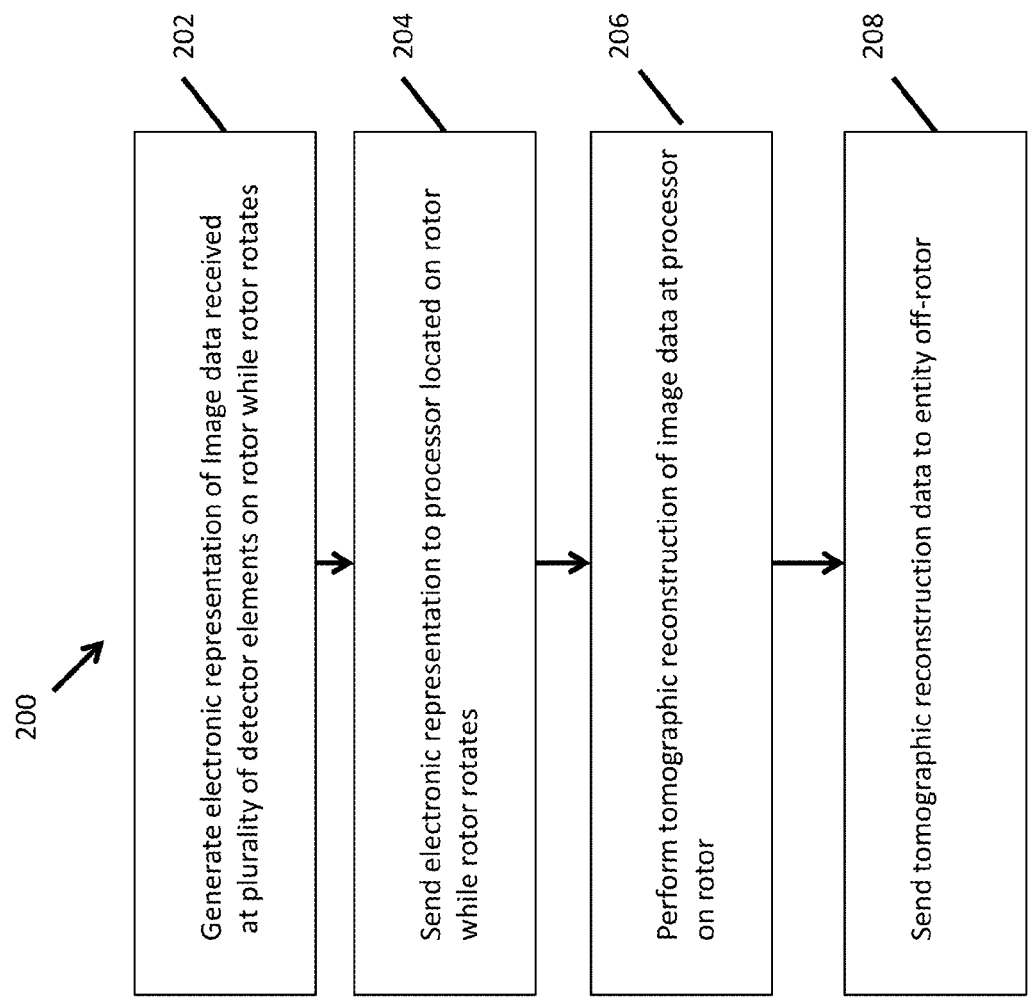
FIG. 2 is a process flow diagram of an embodiment method for generating 3D CT reconstructions.

FIG. 2 is a process flow diagram illustrating an embodiment method 200 for generating 3D CT reconstructions. The method 200 may be performed using an imaging system 100 such as described and illustrated in connection with FIG. 1. In block 202 of method 200, an electronic representation of the image data received at the plurality of detector elements on detector 45 may be generated while the rotor 41 rotates. In embodiments, each detector element may include a x-ray sensitive element, such as a cadmium tungsten crystal, coupled to a photodiode, which may produce an electric charge corresponding to the number of x-ray photons incident on the detector element. Each detector module 107 may include associated electronic components that may be configured read out this charge signal from the photodiode at regular intervals (e.g., 480 Hz). In embodiments, each detector module 107 may further include components, such as one or more analog-to-digital converters, for converting the detector signals to digital signals. In other embodiments, the detector elements may be photon counting type detectors that may directly produce a digital representation of the incident x-ray radiation without requiring separate A/D converters.

In block 204 of method 200, the electronic representation of the image data is sent to the processor 102 located on rotor 41 while the rotor 41 is rotating. In the embodiment of FIG. 1, for example, the electronic representation may be sent to a computer 46 containing a processor 102 and memory 104 which is located on the rotor 41. In various embodiments, the detector modules 107 may include associated electronics for converting the raw image data from each detector element into a form suitable for sending the data to the processor 102. As discussed above, the detector modules 107 may include A/D converter(s) for converting analog signals from the detector elements into digital signals. In embodiments, the digital signals may be provided to the computer 46 and/or processor 102 as a digital video signal, such as in LVDS or camera link format. In some embodiments, the image data signals may be provided to the computer 46 and/or processor 102 in another format, such as gigabit Ethernet. The imaging system 100 may further include a frame grabber, which may be integrated with the computer 46 and may be implemented in hardware, software, or a combination of both. The image data received from the detector 45 may be stored in memory 104 in the form of a plurality of image frames, each of which may represent a combined image of the object from all detector elements/modules in the detector system 45.

In block 206 of method 200, the processor 102 on the rotor 41 may perform tomographic reconstruction of the image data. In embodiments, the processor 102 may be coupled to memory containing processor-executable instructions to perform tomographic reconstruction of the image data received from the detector 45. A variety of tomographic algorithms are known which may be implemented by a processor, as is known in the art. In embodiments, the processor 102 may be a parallel processor comprising a plurality of processing cores for performing the tomographic reconstruction process in parallel. In embodiments, the processor 102 may be a graphics processing unit (GPU), which may be located on a graphics card. The GPU may include a large internal memory (e.g., up to 8 gigabytes or more, such as 2-4 gigabytes) and a plurality of processing cores (e.g., up to 4096 cores or more, such as 2048 cores) for performing parallel processing of the imaging data. The image data (e.g., image frames) from memory 104 may be copied to the GPU memory, and the GPU processor(s) may implement a tomographic algorithm to generate a 3D CT reconstruction of the object.

It will be understood that the processor 102 may include any suitable processing device, such as one or more of a GPU, a CPU, an FPGA, ASIC, etc.

In various embodiments, the tomographic reconstruction at block 206 of method 200 may be performed, at least in part, while the rotor 41 rotating (e.g., during the imaging scan as the detector 45 is acquiring image data). This may save substantial time in generating the reconstruction.

In block 208 of method 200, the reconstruction from processor 102 may be transmitted off of the rotating portion 101 (i.e., the rotor 41) to another entity. As discussed above, the computer 46 may wirelessly transmit tomographic reconstruction data (e.g., 3D images of the object) to the external entity 108, which may be another computer, such as an external workstation, or a separate computer on the imaging system 100 (e.g., a computer on a gimbal that supports the gantry). In other embodiments, the computer 46 may transmit tomographic reconstruction data to another entity using a wired link (e.g., via a slip ring or cable connection to the non-rotating portion 103, or via a data dock to the non-rotating portion 103 in between scans).

In various embodiments, the computer 46 and/or processor 102 may pass the fully reconstructed image off the rotor as soon as the imaging scan is completed. In embodiments, the computer 46 and/or processor 102 may begin passing the reconstruction off the rotor while the imaging system is still scanning. In embodiments, the computer 46 and/or processor 102 may pass the reconstruction off the rotor 41 while the rotor is rotating.

Since the data may be reconstructed while the system 100 is scanning, the most recent images from the reconstruction may be passed off wirelessly while the system is still scanning. The wireless transfer rate may be at least about 300 megabits per second. In embodiments, each image in the reconstruction may be about 4 megabits, thus at least about 75 reconstructed images may be passed off the rotor 41 per second. In one embodiment, the system 100 may scan at least about 24 images per second, and may reconstruct at least about twice that rate (e.g., 48 images per second, or twice real time scan speed). Thus, the system 100 may pass the 24 reconstructed slices per second of scan over a wireless link essentially in real time.

In embodiments, the reconstruction data may be transmitted off the ring via a data dock which may be selectively engaged to provide a connection between the rotating 101 and non-rotating 103 portions of the system 100 when the rotor 41 is not rotating (e.g., between scans). The docking system may include a connector for carrying power between the rotating and non-rotating portions. In embodiments, the docking system may be used to provide power to a power source (e.g., rechargeable battery system) on the rotor 41 such that the power source may be charged using power from an external power source (e.g., grid power). The docking system may also include a data connection to allow data signals to pass between the rotating and non-rotating portions. Further details of a suitable docking system are described in U.S. application Ser. No. 13/441,555, filed Apr. 6, 2012, which has been incorporated herein by reference. In embodiments, a docking system may include, for example, a gigabit Ethernet connection, or similar data connection, that may be used to transmit CT reconstructions off the rotor 41 once the scan is completed and the docking system is engaged. In embodiments, the reconstruction data for an average scan may be about 1000 megabits, so a data dock having a gigabit Ethernet connection may transfer the completely reconstructed data off the rotor 41 in about 1 second for a typical scan.

In embodiments, the system 100 may include a slip ring system that may be configured to pass reconstruction data off the rotor 41 while the system scans. A typical slip ring system may have a data transfer rate that is faster than the scan and reconstruction rates, and thus may pass reconstruction data off the rotor 41 essentially in real time.

In various embodiments, the system 100 may be used to pass "scout" scan data from the rotor 41 in real-time. A scout scan may be performed while the rotor 41 is not rotating to provide a series of scan lines of the patient (e.g., as the source and detector translate along the patient axis), which may be useful, for example, in choosing a subregion to perform a full 3D scan. The scan lines may be provided from the detector 45 to processor 102, as described above, which may transmit the scan lines in real time to an external entity (such as a workstation or other computer) for displaying a 2D image of the patient in real-time.

FIG. 3 illustrates an alternative embodiment system 300 for implementing the method 200 of FIG. 2, in which the 3D tomographic reconstruction may be performed within the detector 45 itself, such as within the detector chassis 303. In this embodiment, a processor 102 and memory 104 may be located within the detector 45, and a separate computer 46 may not be required. Image data may be fed from the detector modules 107 to the memory 104 and processor 102 as described above. The memory 104 and processor 102 may be provided on a graphics card with a GPU, for example. The 3D reconstruction data produced by processor 102 may be transmitted off the rotor 41 from the detector 45, or may be sent to a separate component (e.g., a transmitter/transceiver) outside of the detector 45 for transmission of the rotor 41.

In embodiments, multiple processors 102 with associated memory 104 may be provided in the detector. For example, each module 107 or a subset of modules 107 may include a processor 102 and memory 104 for performing tomographic reconstruction of a portion of the image data (e.g., each module or module subset may backproject its own data). The partially reconstructed data may then be summed, which may be done at a separate processor 102, to provide the full reconstruction, which may then be transmitted off the rotor 41.

It will be understood that in addition to on-board computer 46 and detector 45, the processing device 102 for performing the reconstruction may be at any location on the rotating portion 101 (e.g., rotor 41).

Figure 4:
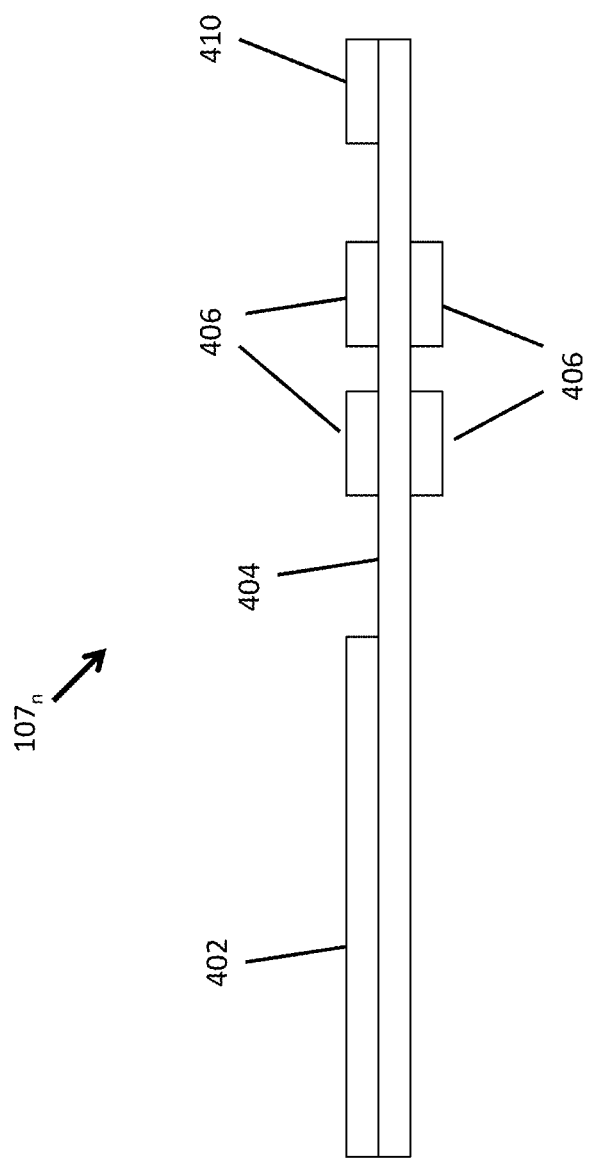
FIG. 4 is a schematic side view of a detector module and associated electronics according to one embodiment.
Figure 5:
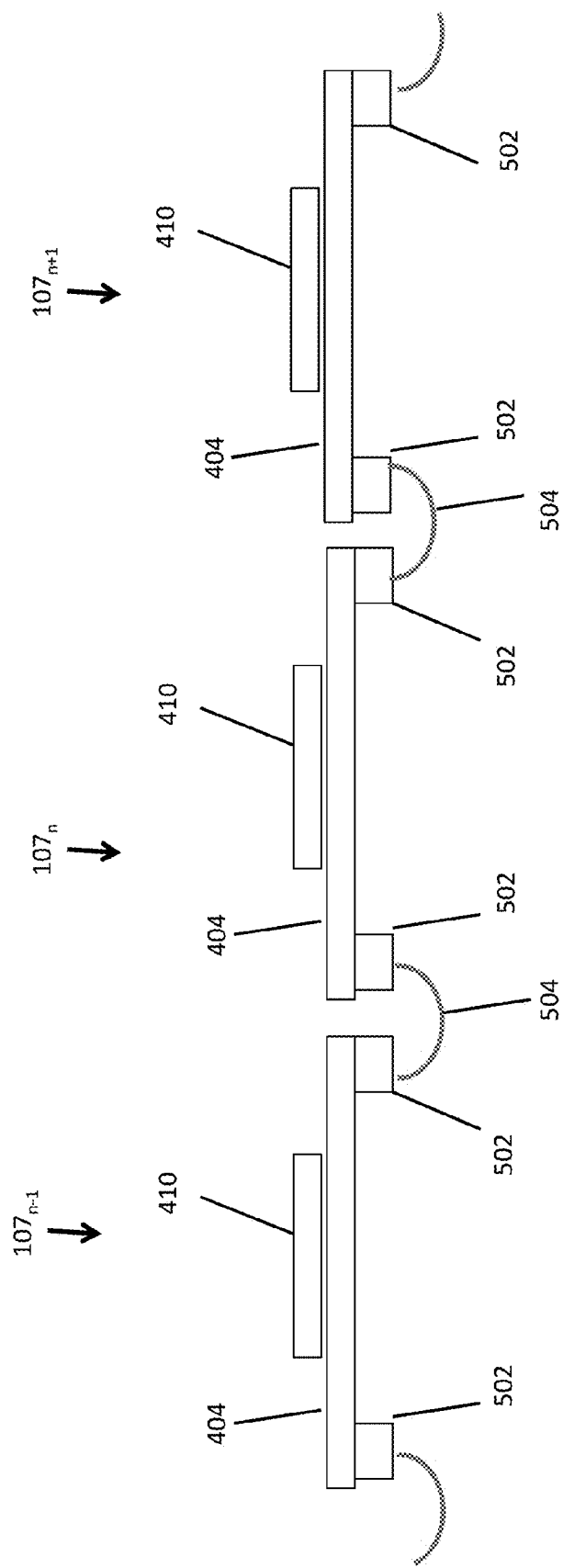
FIG. 5 is a schematic end view illustrating a plurality of detector modules in a daisy-chain configuration.
Figure 6:
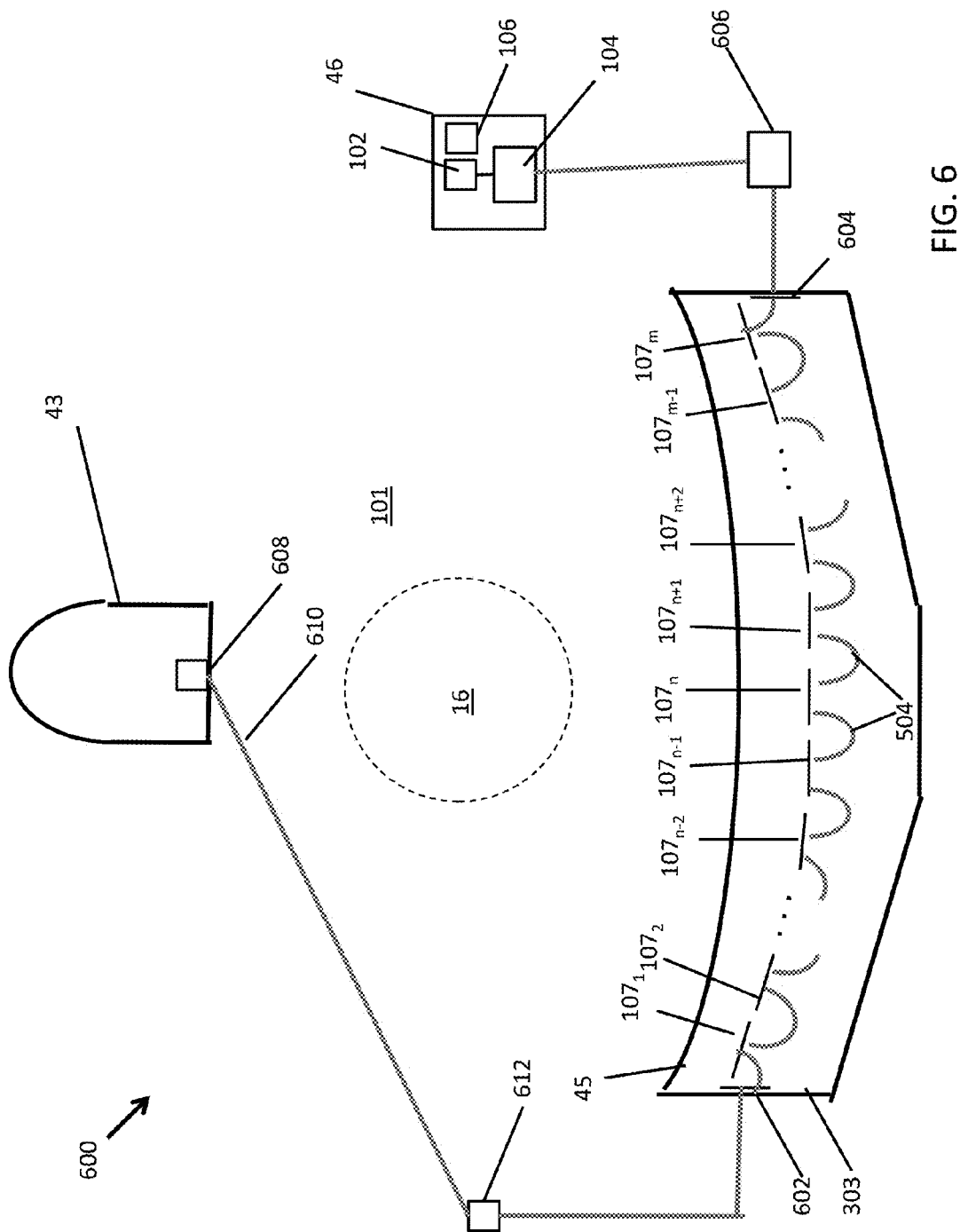
FIG. 6 is a schematic illustration of an imaging system for performing tomographic CT reconstruction on the rotating portion of the system in accordance with one embodiment.

FIGS. 4-6 illustrate further features in accordance with various embodiments. FIG. 4 is a schematic side view of a detector module 107 and associated electronics according to one embodiment, and FIG. 5 is a schematic end view illustrating a plurality of detector modules 107 in a daisy-chain configuration. FIG. 6 is a schematic illustration of an imaging system 600 for performing tomographic CT reconstruction on the rotating portion of the system in accordance with one embodiment.

As shown in FIG. 4, a detector module 107 may include an array of photosensitive elements 402 which may be electrically and optionally physically coupled to a circuit board 404 that may include one or more electronic components. In embodiments, the detector element array 402 may plug into a circuit board 404 using a suitable electronic connection. The circuit board 402 may be configured to couple the raw analog signals from each detector element in the array 402 into an analog-to-digital converter 406 for converting the signal to a digital signal. In the embodiment of FIG. 4, the circuit board 402 includes four A/D converters 406. Each detector element may provide its analog signal over a separate channel into the A/D converters 406. For example, where the array 402 includes 512 pixels, four 128-channel A/D converters 406 may be provided to convert the analog signal from each element into a digital signal.

The A/D converters 406 may include a "double buffering" configuration, such that while a first plurality (e.g., frame) of image data accumulates in one buffer, a second plurality (e.g., frame) of digital image data may be read out. The A/D converters 406 may further output the converted digital data in a suitable digital video format, such as LVDS. In one embodiment, the A/D converters 406 may comprise ADAS1128 analog-to-digital converters from Analog Devices, Inc. of Norwood, Mass.

The circuit board 402 may include a processor 410, which may be, for example, an FPGA. The processor 410 may receive the digital image data from the A/D converters 408, which may be in a digital video format, such as LVDS, and may be programmed to assemble the data into a single image. The processor 410 may be configured to convert the image data to a different digital video format, such as Camera Link. In embodiments, the processor 410 may convert the image data into another suitable format, such as gigabit Ethernet. The processor 410 may also be programmed to receive image data from one or more other detector modules 107, which may be combined with the image data from the A/D converter(s) 406 and passed off of the module 107 in a daisy-chain configuration, as is discussed in further detail below. In preferred embodiments, the processor 410 may receive and transmit the image data in a Camera Link digital video format.

FIG. 5 illustrates three adjacent detector modules $107_{n-1}$, $107_n$, and $107_{n+1}$. Each module may include a circuit board 402 and processor 410 (e.g., FPGA) as discussed above in connection with FIG. 4. Each circuit board 402 may also include a pair of connectors 502, which may be digital video connectors, such as Camera Link digital video connectors. A suitable electrical connection 504, such as a ribbon connector, may be provided between the connectors 502 of each adjacent module 107. Camera Link format may be advantageous due to the small size of the connectors and for clocking issues, although other suitable formats for transmitting the image data, including other digital video formats, may be employed.

FIG. 6 illustrates an imaging system 600 according to one embodiment. A detector 45 includes a plurality of detector modules $107_1$ through $107_m$, which may be as described above in connection with FIGS. 4 and 5. Each detector module may be connected to its adjacent modules via connectors 502, which may be digital video (e.g., Camera Link) connectors. The first module $107_1$ may be similarly connected to a separate circuit board 602 (a "headboard"), which may include a processor (e.g., FPGA). The last module $107_m$ may be similarly connected to a separate circuit board 604 (a "tailboard"), which may also include a processor (e.g., FPGA). The processor of the headboard 602 may generate signals, such as clock signals (e.g., Camera Link clock signals) which may be sent over the digital video connector and propagate down the line of modules 107 in a daisy chain fashion to tailboard 604. The processor of tailboard 604 may similarly generate signals that may propagate back through the line of modules 107 to headboard 602. As discussed above, the processor 410 of each module 107, in response to receipt of a clock signal from headboard 602 and/or in response to receiving image data from another detector module 107, may read out its own image data and transmit the data, which may be in a digital video format such as Camera Link format, to the next detector module 107 in the line. Where the processor 410 of a module 107 receives image data from a prior module 107 in the line, the processor 410 may be configured to combine its own image data with the data of one or more prior modules 107 before passing the combined image data to the next detector module 107 in the line in a daisy-chain configuration.

The combined image data may be received at tailboard 604, which may include a processor configured to transmit the combined data to a computer 46 having a memory 104 and processor 102 and which may be located on the rotatable portion 101 of the system (e.g., mounted to the rotor 41), as is described above in connection with FIGS. 1-3. The processor 102 may be configured to perform tomographic reconstruction of image data that is sent to the computer 46 from the detector modules 107. The tailboard 604 may send the combined image data to the computer 46 in a video signal format, such as Camera Link, or in another format, such as gigabit Ethernet. In embodiments, a video transmitter device 606, such as the iPORT from Pleora Technologies of Ottawa, ON, may be connected to the tailboard 604 for converting the digital video image signal (e.g. Camera Link) into a gigabit Ethernet signal for transmission to the computer 46.

Figure 7:
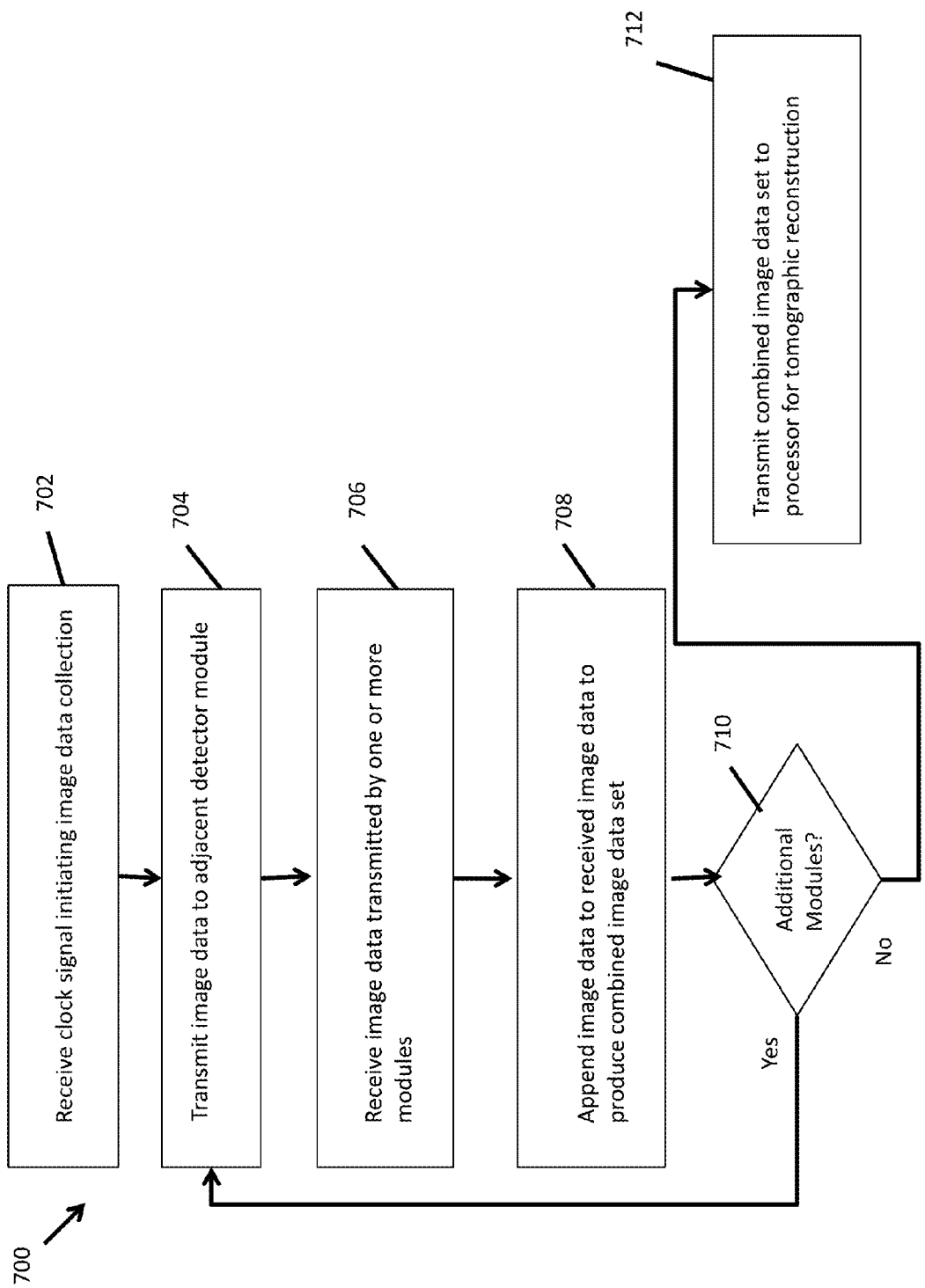
FIG. 7 is a process flow diagram illustrating an embodiment method for performing tomographic CT reconstruction according to one embodiment.

FIG. 7 is a process flow diagram illustrating a method 700 for performing tomographic CT reconstruction according to one embodiment. The method 700 may be performed using an imaging system such as described and illustrated in connection with FIGS. 4-6. In block 702 of method 700, a clock signal may be received at a processor of a first detector module $107_1$ indicating that a set of imaging data is to be collected. The clock signal may be generated by a headboard 602, as described above. In block 704, the processor of the first detector module $107_1$ may transmit digital image data to an adjacent detector module (e.g., $107_2$). The image data may be transmitted in a digital video format, such as Camera Link. In block 706, the digital image data from the first module $107_1$ is received by the processor of the adjacent module $107_2$. In block 708, the processor of the second module $107_2$ may append its own digital image data to the digital image data from the first module $107_1$ to generate a combined digital image data set. The combined digital image data set may be transmitted in a digital video format, such as Camera Link. If there are additional modules with imaging data to transmit (i.e., block 710=Yes), then the combined digital image data set may be sent to the next adjacent module (e.g., $107_3$) in block 704. This process may then be repeated for each detector module (e.g., $107_{n-1}$, $107_n$, $107_{n+1}$, etc.) along the line of detector modules. The combined digital image data set transmitted by each module may be in a digital video format, such as Camera Link. When the last module $107_m$ has appended its own image data to the combined image data set, there are no additional modules to which the combined image data set may be transmitted (i.e., block 710=No). The last module 107. may then transmit the combined image data set to a processor 102 for performing tomographic reconstruction at block 712. As described above, the last module $107_m$ may transmit the combined image data set to the processor 102 via a tailboard 604 and/or a video transmitter device 606 (e.g., iPort). The combined image data set may be transmitted in a digital video format (e.g., Camera Link), and optionally converted into a different format (e.g., gigabit Ethernet) before being received at processor 102/computer 46. The tailboard 604 may optionally send a return signal back through the detector modules 107 to headboard 604 indicating that the combined video image data set has been transmitted to the processor 102. The headboard 604 may then issue another clock signal (e.g., block 702 of method 700), and the entire process may repeat for new image data (e.g., a new frame) collected by the detector modules 107. The process may be repeated at a regular frequency (e.g., 480 Hz) for the entirety of an image scan (e.g., x-ray helical or circular CT scan). The transfer rate of the detector may be variable, and may be more or less than 480 Hz in various embodiments. The clock or frame rate may vary based on the speed of rotation of the rotor 41. For example, for a system that scans at a rate of 1 rotation every two seconds, with 960 frames per rotation, the transfer rate of the detector may be 480 Hz. However, with a faster or slower rotation speed of the rotor 41 the transfer rate of the detectors may be more or less than 480 Hz. In embodiments, between about 500 and 1500 frames may be recorded per rotation of the rotor and the clock or frame rate may be dependent on the speed of rotation of the rotor.

It will be understood that the number of modules (m) in the detector 45 may vary, and modules may be added or removed as needed. In various embodiments, changing the number and/or types of detector modules does not require a new or modified "backplane" electronics board, for example. Also the clock signal (e.g., a Camera Link clock signal) may be variable to provide more or less image frames per second.

As shown in FIG. 6, a reference detector 608 may be provided at the x-ray source 43 to measure the flux of the photons leaving the x-ray tube before the photons impinge on the object being imaged. The reference detector 608 may be a single x-ray sensitive element (e.g., a scintillator, such as a cadmium tungstate crystal), and may be identical to the x-ray sensitive elements in each of the detector elements of the detector system 45. A fiber optic cable 610 may be coupled to the reference detector 608 to transmit an optical signal from the reference detector 608 to an electronics module 612. The electronics module 612 may be located in a temperature-controlled location on the rotor 41 (e.g., in a location where heat from the x-ray source 43 does not interfere with operation of components, such as a photodiode, of the electronics module 612). The reference detector 608, fiber optic cable 610 and electronics module 612 may be potted (e.g., with carbon-filled epoxy) to prevent unwanted light from contaminating the optical signal. The electronics module 612 may include a photodiode that generates an electronic signal in response to the incident optical signal from the reference detector 608, and associated electronics (e.g., A/D converter, FPGA, etc.) that may convert the electronic signal into a digital signal that may be fed to the processor 102 for use in performing the tomographic reconstruction. The reference detector signal may be sent in a digital video format, such as Camera Link. In embodiments, the digital reference detector signal from the electronics module 612 may be sent to the detector 45, where the signal may be embedded within the digital image data from the detector modules 107 before it is transmitted to the processor 102 for reconstruction. For example, the reference detector signal may be sent to the headboard 602 of the detector 45. The headboard 602 may then send the signal to the first detector module $107_1$, such as with its clock signal, and the reference detector signal may be appended to the digital image data from the first detector module $107_1$ when it is transmitted to the next module $107_2$ along the line. The reference detector signal may thus propagate down the line of detector modules 107 in a daisy-chain fashion, and may then be fed to the processor 102 for tomographic reconstruction.

The reference detector 608 may also include a temperature sensor, such as a resistance temperature detector (RTD) that may generate an electronic signal indicative of the temperature within the x-ray source 43. The temperature signal may be a digital signal that may be embedded within the image data stream that is sent to the processor 102 for tomographic reconstruction in the manner described above for the reference detector signal.

Figure 8:
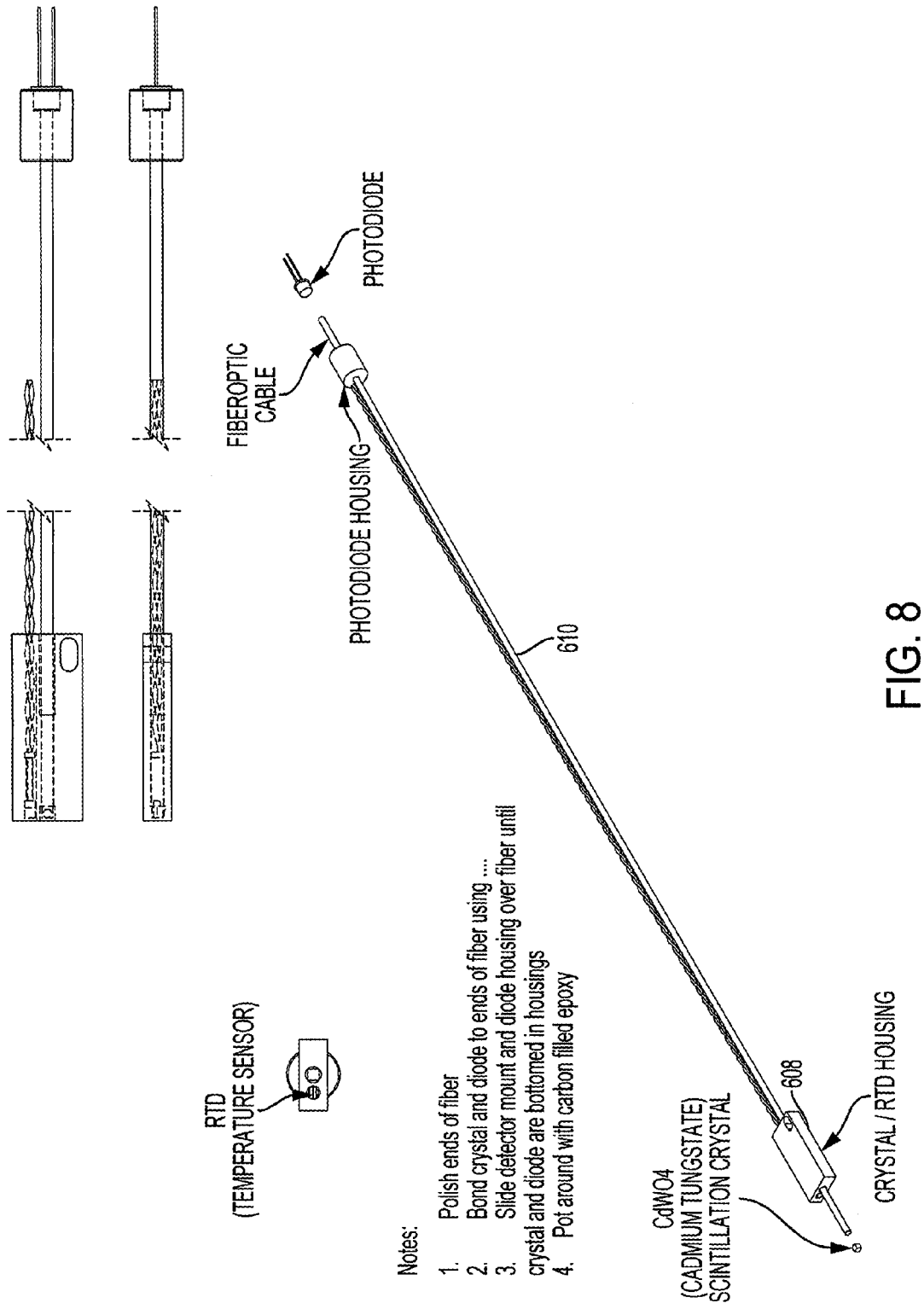
FIG. 8 illustrates a reference detector according to one embodiment.

FIG. 8 illustrates a reference detector 608 and fiber optic cable 610 assembly according to one embodiment. The reference detector 608 may be embedded in a housing, which may be a brass housing having a hole for x-ray photons to enter. An RTD may also be provided in the housing. The fiber optic cable 610 may have a polished first end that is bonded to a polished end of the reference detector 608 (e.g., scintillator crystal) for receiving incident light from the reference detector 608. The subassembly of reference detector 608 and fiber optic cable 610 may inserted into the housing (along with the RTD) and potted within the housing, which may be a brass housing. The fiber optic cable 610 may have a polished second end that may be bonded to a photodiode. One or more wire leads may couple the RTD output to an electronics module (e.g., circuit board).

Figure 9A:
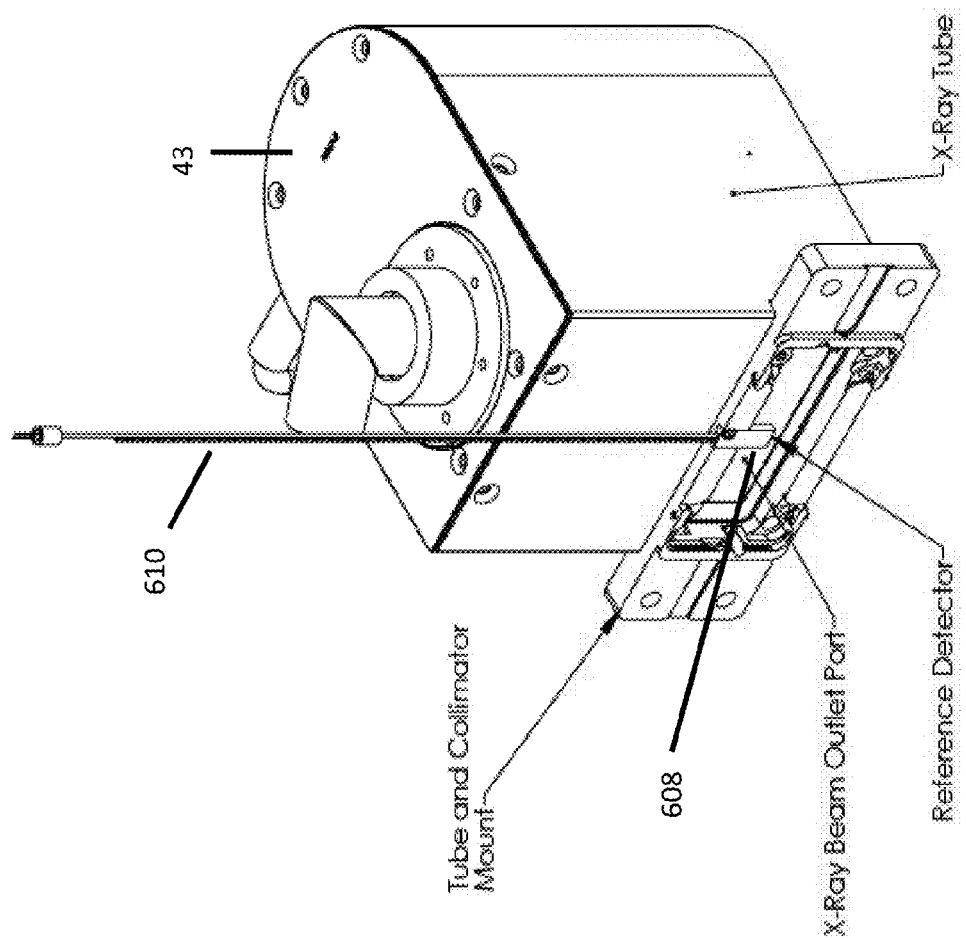
FIGS. 9A and 9B illustrate a reference detector assembly positioned in an X-ray tube according to one embodiment.
Figure 9B:
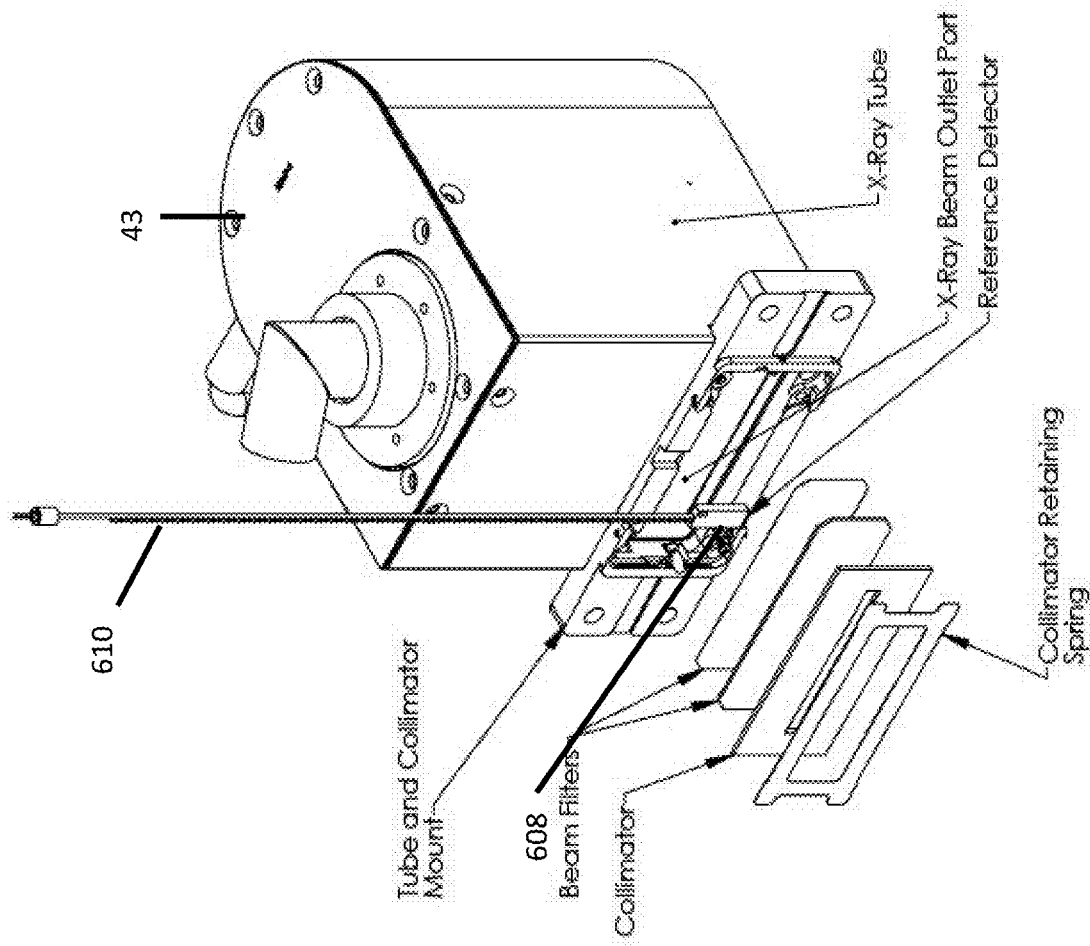

FIGS. 9A and 9B illustrate the reference detector 608 and fiber optic cable 610 assembly within an x-ray source 43. As is illustrated in FIGS. 9A and 9B, the reference detector 608 may be positioned proximate to an edge of the x-ray beam outlet port, such that the reference detector 608 does not cast a "shadow" on the object being imaged. The reference detector 608 may be positioned behind a collimator so that it may measure the flux of the x-ray photons prior to the photons being collimated.

The foregoing method descriptions are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not necessarily intended to limit the order of the steps; these words may be used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored on as one or more instructions or code on a non-transitory computer-readable medium. The steps of a method or algorithm disclosed herein may be embodied in a processor-executable software module executed which may reside on a non-transitory computer-readable medium. Non-transitory computer-readable media includes computer storage media that facilitates transfer of a computer program from one place to another. A storage media may be any available media that may be accessed by a computer. By way of example, and not limitation, such non-transitory computer-readable storage media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of non-transitory computer-readable storage media. Additionally, the operations of a method or algorithm may reside as one or any combination or set of codes and/or instructions on a machine readable medium and/or computer-readable medium, which may be incorporated into a computer program product.

The preceding description of the disclosed aspects is provided to enable any person skilled in the art to make or use the present invention. Various modifications to these aspects will be readily apparent to those skilled in the art, and the generic principles defined herein may be applied to other aspects without departing from the scope of the invention. Thus, the present invention is not intended to be limited to the aspects shown herein but is to be accorded the widest scope consistent with the principles and novel features disclosed herein.

What is claimed is:

1. An x-ray CT system, comprising:
   a rotor;
   a gantry defining a central imaging bore and comprising a housing within which the rotor rotates around the bore;
   an x-ray source mounted to the rotor; and
   a detector system mounted to the rotor, the detector system comprising:
   a detector chassis comprising a rigid frame;
   a plurality of detector elements within the detector chassis and arranged on the rigid frame; and
   a processing unit located on or in the detector chassis and comprising a plurality of processing cores for performing parallel processing of image data received from the plurality of detector elements to generate a three-dimensional tomographic reconstruction of an object located in the bore.

2. The x-ray CT system of claim 1, wherein the processing unit comprises a graphics processing unit (GPU).

3. The x-ray CT system of claim 2, wherein the GPU comprises an internal memory of at least 2 gigabytes and at least 2048 processing cores.

4. The x-ray CT system of claim 1, wherein the tomographic reconstruction is at least partially generated while the rotor rotates around the bore.

5. The x-ray CT system of claim 1, further comprising a wireless transmitter coupled to the processing unit that transmits the tomographic reconstruction from the rotor to an entity off the rotor.

6. The x-ray CT system of claim 1, wherein the detector system comprises a plurality of detector modules arranged on the rigid frame, each detector module including an array of detector elements of the plurality of detector elements and associated electronic components configured to read out image data from the array of detector elements.

7. The x-ray CT system of claim 1, wherein the plurality of detector modules are connected in series in a daisy-chain configuration.

8. The x-ray CT system of claim 7, wherein each detector module includes a processor configured with processor-executable instructions to read out image data from the array of detector elements on the module and transmit the image data from the detector module in response to receiving at least one of a clock signal and image data from a preceding detector module of the series of detector modules.

9. The x-ray CT system of claim 8, wherein the processor of each detector module is configured with processor-executable instructions to combine image data from the detector module with image data received from one or more preceding detector modules of the series of detector modules before transmitting the combined image data from the detector module.

10. The x-ray CT system of claim 9, wherein the combined image data is transmitted to each subsequent detector module of the series of detector modules for adding additional image data, and the combined image data from all of the detector modules of the series is transmitted to the processing unit of the detector system for generating the tomographic reconstruction.

11. The x-ray CT system of claim 9, further comprising:
a reference detector comprising a detector element that is positioned to measure a flux of photons emitted by the x-ray source before the photons impinge on the object located within the bore, the reference detector located at least partially outside of the detector system and comprising an electronics module that generates an electronic representation of the measurement of the flux of photons emitted by the x-ray source, wherein the electronic representation of the measurement of the flux of photons is sent to the processing unit in the detector system for use in generating the tomographic reconstruction.

12. The x-ray CT system of claim 11, wherein the reference detector comprises a housing containing the detector element located proximate to an x-ray beam outlet port of the x-ray source and a fiber optic cable coupled to the detector element to transmit an optical signal from the detector element to the electronics module, wherein the electronics module is located on a temperature-controlled area of the rotor.

13. The x-ray CT system of claim 12, wherein the electronics module comprises a photodiode that converts the optical signal from the detector element to an electronic signal that is transmitted to the processing unit in the detector system.

14. The x-ray CT system of claim 11, wherein the reference detector comprises a temperature sensor that generates an electronic signal indicative of a temperature within the x-ray source, wherein the electronic signal indicative of a temperature within the x-ray source is sent to the processing unit in the detector system for use in generating the tomographic reconstruction.

15. A method for generating an x-ray CT reconstruction with an imaging system comprising an x-ray source and a detector system mounted to a rotatable rotor, the method comprising:
generating an electronic representation of image data received at a plurality of detector elements of the detector system while the rotor rotates;
sending the electronic representation of image data to a processing unit located on or in the detector chassis while the rotor rotates;
performing parallel processing of the image data using a plurality of processing cores of the processing unit to generate a three-dimensional tomographic reconstruction; and
transmitting the tomographic reconstruction from the rotor to an entity off the rotor.

16. The method of claim 15, wherein the processing unit comprises a graphics processing unit (GPU).

17. The method of claim 16, wherein the GPU comprises an internal memory of at least 2 gigabytes and at least 2048 processing cores.

18. The method of claim 15, further comprising generating the tomographic reconstruction while the rotor is rotating.

* * * * *